United States Patent
Nam et al.

(12) 
(10) Patent No.: US 6,265,001 B1
(45) Date of Patent: Jul. 24, 2001

(54) RICE BASED BEVERAGE PRODUCT AND PROCESS FOR MAKING THE SAME

(76) Inventors: Sung-Hee Nam, 553-3 Gueui-dong, Kwangjin-ku, Seoul; Jang-Ho Seo, 101-1310 Usung-Apt, 738 Gongneug-dong, Nowon-ku, Seoul; Mi-La Kim, 29-403 Youngdong-Apt, Yoksam 2-dong, Kangnam-ku, Seoul; Mi-Jung Kim, 301 Hanshinvilla, 278-10 Gyebong 3-dong, Kuro-ku, Seoul, all of (KR)

( * ) Notice: Subject to any disclaimer, the term of this patent is extended or adjusted under 35 U.S.C. 154(b) by 0 days.

(21) Appl. No.: 09/491,303

(22) Filed: Jan. 25, 2000

(51) Int. Cl.$^7$ ........................................................ A23L 2/38
(52) U.S. Cl. ................................ 426/29; 426/52; 426/598
(58) Field of Search ................................ 426/49, 50, 52, 426/28, 29, 30, 590, 598, 627, 51

(56) References Cited

U.S. PATENT DOCUMENTS 4,857,339 * 8/1989 Maselli et al. ........................ 426/28
5,667,835 * 9/1997 Osajima et al. ...................... 426/521

FOREIGN PATENT DOCUMENTS 55-138368 * 10/1980 (JP) .

* cited by examiner

*Primary Examiner*—Keith Hendricks
(74) *Attorney, Agent, or Firm*—Lee & Hong

(57) ABSTRACT

Disclosed is the beverage product made of rice and the method for making the same. The method comprises A method of producing a beverage, comprising the steps of roasting the polished and unpolished rice; dividing the rice into particles of reduced size; mixing the rice with refined water; treating the rice with bacteria alpha-amylase whereby gaining a first reaction product; treating the first reaction product with glucoamylase, protease, and pectinase whereby gaining a second reaction product; deactivating the second reaction product; refining the second reaction product; and treating the second reaction product with sucrose fatty acid ester and refined water under uniform pressure of between 130 and 150 bar whereby being emulsified and homogenized.

9 Claims, No Drawings

RICE BASED BEVERAGE PRODUCT AND PROCESS FOR MAKING THE SAME

FIELD OF THE INVENTION

The present invention relates to a beverage product containing unpolished rice and polished rice and a method of producing the same.

The need for improved nutritious food supplements is greatly increasing as the public becomes more health and weight conscious. And many beverages containing rice have been suggested, one of which is a fermented rice punch. The rice punch uses polished rice whose embryo bud is removed through polishing process. Compared to the unpolished rice, the polished rice lacks vitamin B group, mineral, essential amino acid, and the like, which may cause a modern disease. Therefore it is preferable to use unpolished rice for the nutritious beverages.

To meet the needs, the beverages containing unpolished rice as well as polished rice have been developed, but they are made through a fermentation process by steaming the rice, or a sterilization process at high pressure in a retort, which requires high production cost. The high temperature and high pressure process performed in the retort reduces the freshness and nutritive value of the product.

SUMMARY OF THE INVENTION

Therefore, it is an object of the invention to provide a fresh and nutritious beverage.

It is also an object of the invention to provide a method for producing the beverage, which can reduce the production cost.

To achieve the objects, the present invention provides a method of producing a beverage which includes the steps of roasting the polished and unpolished rice; dividing the rice into particles of reduced size; mixing the rice with refined water; treating the rice with bacteria alpha-amylase whereby gaining a first reaction product; treating the first reaction product with glucoamylase, protease, and pectinase whereby gaining a second reaction product; deactivating the second reaction product; refining the second reaction product; and treating the second reaction product with sucrose fatty acid ester and refined water under uniform pressure of between 130 and 150 bar whereby being emulsified and homogenized.

The rice is preferably roasted for 10 to 20 minutes. The amount of the polished rice in the product is more than that of the unpolished rice, since taste of the polished rice becomes the consumers more than the unpolished.

It is another characteristic of the invention that the homogenized product is sterilized for several seconds.

It is still characteristic of the invention that the pH of the beverage is between 3.2 and 6.7.

DETAILED DESCRIPTION OF THE PREFERRED EMBODIMENT $1^{st}$ Process-roasting

First, the white or polished and brown or unpolished rice is carefully selected and roasted at temperature of 150 to 200 for 10 to 20 minutes, and flavor and the color is given to the rice. At this time, if the roasting temperature is lower than 150, it will require longer time and the color and the flavor of the rice is not so good. And if the temperature is over 230, the rice is ready to be burnt. Thus the roasting temperature is carefully selected.

$2^{nd}$ Process-agitation

The white and the brown rice of the 1st process is reduced to powder to a size of between 10 and 50 mesh and mixed in the predetermined ratio. Then among the mixed rice from 8 to 20 wt % of weight of the predetermined product is chosen and is defined as a starting material, which is mingled by refined water of between 4 and 8 times of the weight of the starting material and agitated at about 100. The mingled solution is a starting solution in this production method The weight ratios of brown rice to the white rice are from 1:9 to 35:5, preferably to 1:9 to 2:8. If too much brown rice is present, the production cost will increase.

$3^{rd}$ Process-first Treatment with Enzyme

The agitated material is cooled to between 90 and 100, and is treated for 10 to 30 minutes with bacteria alpha amylase of 0.02–0.06 wt. %. The reaction product of this process has saccharinity of between 6 and 11 Brix.

$4^{th}$ Process-second Treatment with Enzyme

The reaction product of the $3^{rd}$ process is again cooled to 50–60, and treated with 0.05 to 0.25 wt. % glucoamylase, 0.1 to 0.3 wt. % protease, and 0.05 to 0.25 wt. % pectinase for 3 to 8 hours. The reaction process of this process has saccharinity of between 8 to 13 Brix.

$5^{th}$ Process-deactivation of Enzyme

The reaction product of the $4^{th}$ process is then heated to about 100 for 5 to 10 minutes to deactivate the enzymes.

$6^{th}$ Process-refinement

The result solution of $5^{th}$ process is strained through a strainer of size of 40–120 mesh and the remainders of the solution are removed after a centrifugal separator process. Then clean and clear solution is obtained. The refined solution is more than 80 wt. % of the starting solution and has saccharinity of between 11 and 13 Brix.

$7^{th}$ Process-homogenized Emulsification Process

The solution which includes 40 to 65 wt % the refined solution, 57.018–27.35 wt % refined water, 2–6 wt % sugar or inverted sugar, 0.002–0.2 wt % vitamin C or citric acid, 0.1–0.8 wt % bean oil, 0.08–0.25 wt % palm oil, and 0.2–0.4 wt % sucrose fatty acid ester is then homogenized and emulsified under a uniform pressure of 130 to 150 bar. The emulsification process is performed 1–3 times to homogenize the solution uniformly.

The homogenized emulsification and mixing with sucrose fatty acid ester which has a bacterostatic ability enhances the sterilizing power and makes the product yellow or light yellow. The pH of emulsified solution is between 3.2 and 6.7 and is sterilized at a temperature from about 115 to about 128 for 20 to 40 seconds without being sterilized in a retort. The sterilized product is then filled in a bottle or polyethylen terephthalate container at a temperature from 85 to 95.

Since the sterilization time is short, the product can maintain its freshness and its nutritive value.

$8^{th}$ Process-packing

Sterilization is conducted to the container having the product in at a temperature more than 85 for 10 to 20 minutes. After that it is cooled to 30 to 34 and packed.

As described above the processes according to the invention does not use retort-sterilization, which requires high temperature and high pressure, thus the processing time also can be reduced.

Also this method does not need large amount of cooling water and energy.

What is claimed is:

1. A method of producing a beverage, the method comprising the steps of:
   roasting polished and unpolished rice;
   reducing the rice into powder;
   mixing the rice with water;
   treating the rice with bacterial alpha-amylase whereby gaining a first reaction product;
   treating the first reaction product with glucoamylase, protease and pectinase whereby gaining a second reaction product;
   deactivating the second reaction product by heating;
   refining the second reaction product by straining; and
   treating the second reaction product with sucrose fatty acid ester and water and emulsifying and homogenizing under uniform pressure of between 130 and 150 bar.

2. The method of claim 1, wherein the roasting is done for 10 to 20 minutes.

3. The method of claim 1, wherein the amount of the polished rice is more than that of the unpolished rice.

4. The method of claim 1, further comprising, sterilization of the homogenized product for several seconds.

5. The beverage product made by the process of claim 1.

6. The beverage product made by the process of claim 2.

7. A method of producing a beverage using a roasted and powdered rice, the method comprising the steps of:
   mixing roasted and powdered rice with water;
   treating the rice with bacterial alpha-amylase to produce a first reaction product;
   treating the first reaction product with glucoamylase, protease and pectinase to produce a second reaction product;
   heating the second reaction product;
   filtering the second reaction product; and
   treating the second reaction product with sucrose fatty acid ester and water, and emulsifying and homogenizing under uniform pressure of between about 130 and 150 bar.

8. The method of claim 7, wherein the roasting is done for 10 to 20 minutes.

9. The beverage product made by the process of claim 7.

* * * * *